United States Patent [19]

Brouwer et al.

[11] Patent Number: 5,134,144
[45] Date of Patent: Jul. 28, 1992

[54] PESTICIDAL 3-ARYLPYRIMIDINYL ETHERS AND THIOETHERS

[75] Inventors: Walter G. Brouwer, Guelph; Ethel E. Felauer, Puslinch, both of Canada; Paul T. McDonald, Middlebury; James A. McGuinness, Naugatuck, both of Conn.; Anupama Mishra, Guelph, Canada

[73] Assignees: Uniroyal Chemical Company, Inc., Middlebury, Conn.; Uniroyal Chemical Ltd./Ltee, Elmira, Canada

[21] Appl. No.: 439,732

[22] Filed: Nov. 20, 1989

[51] Int. Cl.$^5$ .................. C07D 239/54; A01N 43/54
[52] U.S. Cl. .................................... 514/274; 544/314
[58] Field of Search ..................... 544/314; 514/274

[56] References Cited

U.S. PATENT DOCUMENTS

| | | | |
|---|---|---|---|
| 4,280,999 | 7/1981 | Steelman et al. | 424/251 |
| 4,394,383 | 7/1983 | Kawata | 424/285 |
| 4,746,352 | 5/1988 | Wenger et al. | 71/90 |
| 4,760,163 | 7/1988 | Wenger et al. | 560/34 |
| 4,954,635 | 9/1990 | Rosario-Jansen | 548/354 |
| 4,988,719 | 1/1991 | Wagner | 514/369 |

OTHER PUBLICATIONS

Wenger et al., Chemical Abstracts, vol. 109, entry 231048g (1988).

*Primary Examiner*—John M. Ford
*Attorney, Agent, or Firm*—Glenn E. Karta

[57] ABSTRACT

This invention is related to a novel class of 3-arylpyrimidine ethers and thioethers having insecticidal, miticidal and nematocidal activity at low concentration. The class of compounds is represented by formula (I):

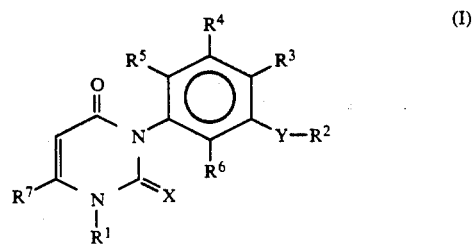

wherein $R^1$, $R^2$, $R^3$, $R^4$, $R^5$, $R^6$, $R^7$, X and Y have the significance given in the description.

Pesticidal compositions, methods of controlling pests and methods for preparing the compounds are within the scope of the invention.

8 Claims, No Drawings

PESTICIDAL 3-ARYLPYRIMIDINYL ETHERS AND THIOETHERS

BACKGROUND OF THE INVENTION

1. Field of the Invention

The present invention is directed to a class of aryl pyrimidines and derivatives thereof. More specifically, the present invention is directed to a class of phenyl pyrimidine derivatives useful as insecticides, miticides and nematocides, particularly useful against rice planthopper.

2. Description of Related Art

Commercially important food, fiber and ornamental plants are continually subjected to the devastation caused by insect, mite and nematode pests. This represents a serious economic threat, particularly to such important grain plants as rice and corn. For this reason there is a continuing need for the development of new more effective insecticides, miticides and nematocides, especially ones that are effective at low dosages. Such pesticides combine the necessary control of insects, mites and nematodes without attendant environmental difficulties.

The utilization of aromatic substituted pyrimidines having insecticidal properties is well known in the art. One such disclosure in U.S. Pat. No. 4,280,999, which describes 5-chloro-3-phenyl-6-methyluracil as having insecticidal properties against certain insect pests. Most of the chemicals disclosed in this patent posses alkyl substitution at position 3 of the pyrimidine ring and biological data is only given for a single alkylated compound, i.e., 5-bromo-3-secbutyl-6-methyl uracil. Specifically, U.S. Pat. No. 4,280,999 discloses that insects of the family Culicidae, e.g., mosquitoes, are controlled at relatively high dosage rates.

U.S. Pat. No. 4,746,352 and its divisional, U.S. Pat. No. 4,760,163, disclose certain 3-(5-carboxy-4-(halo or nitro substituted)-phenyl) uracil esters and salts having herbicidal properties Insecticidal activity is not disclosed.

A new class of compounds have now been discovered which have particular pesticidal application as insecticides, miticides and nematocides being particularly effective against pests which attack commercially important grain plants, but which are so active that they can be applied in low concentrations.

SUMMARY OF THE INVENTION

A novel class of 3-aryl pyrimidinyl ethers and thioethers having outstanding insecticidal, miticidal and nematocidal activity, particularly against rice plant hoppers; methods for preparing same; and pesticidally active compositions containing same are disclosed. The compounds are represented by the formula:

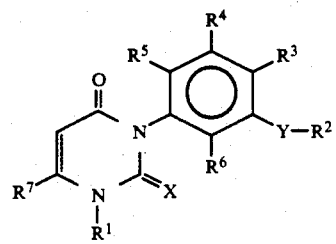

wherein the substituents $R^1$ through $R^7$ inclusive, X and Y are as hereinafter described.

DETAILED DESCRIPTION OF THE INVENTION

The invention relates to insecticidally, miticidally and nematocidally active compounds of the formula:

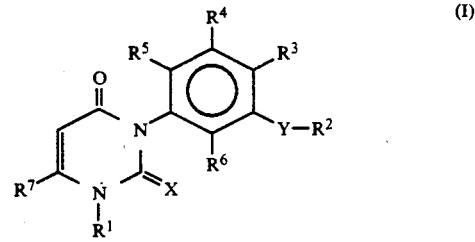

wherein
- $R^1$ is hydrogen, alkali or alkaline earth metal or organic base salts;
- $R^2$ is $C_1$-$C_6$ hydrocarbyl or $-CR^8C^9-CO_2R^{10}$ wherein
  - $R^8$ and $R^9$ are each independently hydrogen or linear or branched $C_1$-$C_4$ alkyl and $R^{10}$ is hydrogen or $C_1$-$C_6$ hydrocarbyl;
- $R^3$ is hydrogen, haloqen, nitro, $C_1$-$C_6$ hydrocarbyl, $C_1$-$C_6$ alkoxy, $C_1$-$C_6$ alkylthio or $C_3$-$C_6$ cycloalkyl;
- $R^4$, $R^5$ and $R^6$ are each independently hydrogen, halogen, $C_1$-$C_4$ alkyl or $C_1$-$C_4$ alkoxy;
- $R^7$ is $C_1$-$C_6$ halogenated hydrocarbyl residue; and X and Y are each independently oxygen or sulfur. By hydrocarbyl is meant a linear, branched or cyclic, saturated or unsaturated moiety containing only hydrogen and carbon atoms.

Preferably,
- $R^1$ is hydrogen or potassium;
- $R^2$ is $C_1$-$C_4$ hydrocarbyl or $-CR^8R^9-CO_2R^{10}$ wherein $R^8$ and $R^9$ are each independently hydrogen or linear or branched $C_1$-$C_4$ alkyl and $R^{10}$ is hydrogen or $C_1$-$C_4$ alkyl;
- $R^3$ is hydrogen, halogen, $C_1$-$C_4$ alkyl, $C_1$-$C_4$ alkoxy or $C_1$-$C_4$ thioalkyl;
- $R^4$, $R^5$ and $R^6$ are each independently hydrogen, halogen, $C_1$-$C_4$ alkyl or $C_1$-$C_4$ alkoxy;
- $R^7$ is $C_1$-$C_3$ fluorinated alkyl;
- X is oxygen or sulfur; and
- Y is oxygen.

Most preferably,
- $R^1$ is hydrogen;
- $R^2$ is $C_1$-$C_3$ hydrocarbyl or $-CH_2CO_2R^{10}$ wherein $R^{10}$ is $C_1$-$C_4$ alkyl;
- $R^3$ is hydrogen, chloro, methyl or methoxy;
- $R^4$, $R^5$ and $R^6$ are hydrogen, fluoro or methoxy;
- $R^7$ is trifluoromethyl; .
- X is oxygen or sulfur; and
- Y is oxygen.

In another aspect, this invention relates to insecticidal, miticidal and nematocidal compositions (hereinafter pesticidal compositions) comprising:

(A) a pesticidally effective amount of a compound having the structure of formula (I); and (B) a suitable carrier.

In yet another aspect, this invention relates to a method of controlling insects, mites and nematodes, which method comprises applying to the locus a pesticidally effective amount of a composition comprised of:
(A) a pesticidally effective amount of a compound having a structure in accordance with formula (I), and
(B) a suitable carrier.

In a further aspect, this invention relates to a process for preparing a compound of formula (I) wherein $R^1$ through $R^7$, X and Y have the meanings given for formula (I), which process comprises the following retrosynthetic scheme:

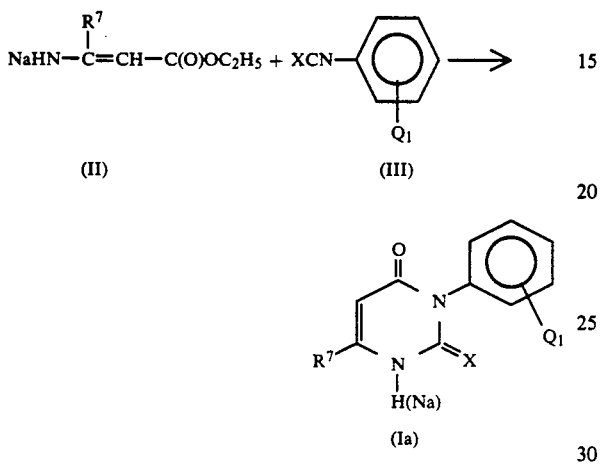

A suitable sodium salt of an enamine (II) is reacted with an isocyanate or isothiocyanate (III) at low temperature, typically between −50° C. and −70° C. in an inert solvent such as tetrahydrofuran or dimethylformamide and the reaction allowed to come to ambient temperature over several hours. The pyrimidine (Ia) is isolated by first removing the solvent, dissolving the residual mixture in water and acidifying with mineral acid.

The class of compound represented by (II) are made by methods known in the literature. Starting materials are beta-keto esters which furnish the enamines by reaction with ammonia gas. Their sodium salts are made by adding the enamines to a suspension of sodium hydride in a suitable solvent like tetrahydrofuran or dimethylformamide.

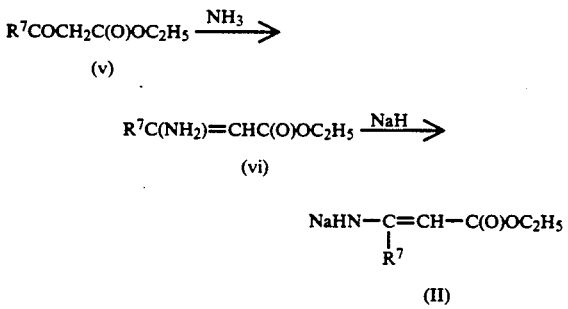

where $R^7$ and X are as defined above and $Q_1$ represents the substitution pattern on the aromatic ring of structure formula (I).

The isocyanates and isothiocyanates of type (III) are made separately by reacting a suitable aromatic amine (IV) with phosgene or thiophosgene.

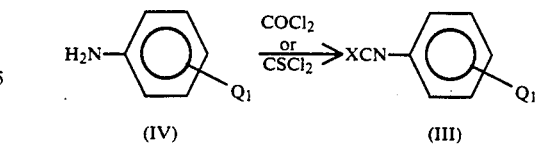

Organic base salts are made by treating the compounds of formula (I), $R^1$ TM H with an organic base of the formula R' R'' R''' N, wherein one of the R', R'' and R''' is a hydrocarbyl or hydroxyalkyl group having from 1 to 24 atoms, or two or three of the R' R'' and R''' groups form a basic nitrogen-containing heterocyclic moiety, and the remaining substitutents are hydrogen, in a suitable solvent, e.g., alcohol or tetrahydrofuran. In general, the organic base has to have sufficient strength to form a salt, i.e., the pKa of the base has to be greater than about 4.85. Removal of the solvent leaves the organic base salt of the compounds of the invention, that is

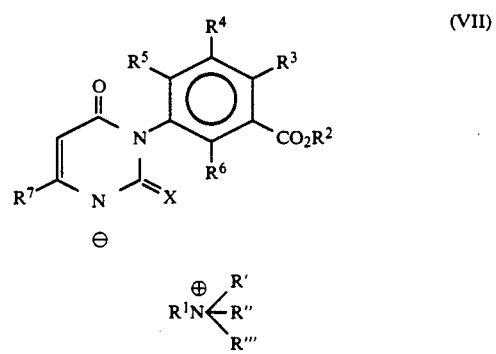

The pesticidal compositions of the present invention, as stated above, employ compounds of structural formula (I) in combination with a carrier. The carriers, may be a finely divided or granular organic or inorganic inert material. Among the inert carriers are attapulgate clay, sand, vermiculite, corncobs, activated carbon and mineral silicates such as mica, talc, pyrophyllite and clays.

In another preferred embodiment, the composition comprises a solution. That is, the active agent, a compound whose structural formula is (I), is dissolved in a suitable solvent which acts as the carrier. Among the solvents, acting as carrier, are acetone, methanol, isopropanol, t-butyl alcohol, cyclohexanol, n-butyl alcohol, cyclohexanone, toluene, xylene, dioxane, methylformamide, dimethylsulfoxide, ethylene dichloride and N-methylpyrrolidone.

In still another preferred embodiment the composition comprises a water emulsion carrier. The emulsion is prepared from a solution as described immediately above. To the solution is added a surface active agent. Surface active agents suitable for use in forming the emulsion are known to those skilled in the art. McCutcheon's Detergents and Emulsifiers, Allured Publishing Corp., Ridgewood, N.J. (1970); U.S. Pat. No. 2,514,916, Columns 2 to 4; and U.S. Pat. No. 2,547,734, Columns 3 and 4 provide detailed examples of such surface active agents. These agents may be anionic, non-ionic or cationic.

In yet still another preferred embodiment the composition employs a dispersant as carrier. In this embodiment, a compound of structural formula (I), is mixed with a solvent of the type described above to form a solution which is added to one of the above-described surface active agents and water.

In still another embodiment, the active compound is premixed with an inert solid carrier which is added to a surface active agent with water to provide another form of dispersion.

The above embodiment may alternatively be employed in non-liquid form. That is, the composition may take the form of a dust, granules, a paste or a wettable powder. In these embodiments, the active compound having the structural formula (I), is admixed with the inert carrier to form a solid composition. Thus, for example in the embodiment wherein a powder is formed, the solid inert carrier is provided in powder form. In many such cases, the inert carrier is a mineral silicate. The solid may be made wettable by the addition of a surface active agent.

In another principal application, an aerosol is prepared by dissolving the active compound in a first solvent. This first solvent is conventional in the sense that although it is volatile, it is not highly volatile. This solution is then admixed with a highly volatile solvent, a so-called liquid aerosol carrier. The aerosol carrier is liquid only under elevated pressure. At ordinary temperatures and at atmospheric pressure the aerosol carrier is a gas. In a sub-embodiment of this preferred embodiment the aerosol carrier may itself be active. For example the carrier may be an insecticide, a herbicide, a bactericide or a plant growth regulant.

In a preferred embodiment of a method of the present invention, a method for controlling insects, mites and nematodes, the insects particularly amenable to control by a compound having the structural formula (I), are rice planthopper, *Sogatodes oryzicola*. Rice planthopper control has been found t be extremely effective at low dose rates.

The following examples are given to illustrate the scope of the present invention. Because these examples are given for illustrative purposes only, the invention embodied herein should not be limited to the actual examples provided.

EXAMPLE 1

2,3-Dihydro-3-[3-(1-methylethoxy)-4-methylohenyl]-2-thioxo-6-(trifluoromethyl)-4(1H)-pyrimidinone 2-methyl-5-nitroaniline (40 g) was dissolved in refluxing 10% sulphuric acid (600 ml), cooled to 0° C. whereupon the salt separates out. With continuous stirring, sodium nitrite solid (18 g) was added in small portions. The diazitization was complete when a positive starch/KI test was observed. This diazonium solution was added at once to a vigorously refluxing solution of water (800 ml) and concentrated sulphuric acid (400 ml). Refluxing was continued until all gassing had ceased. A solid had precipitated out and, upon cooling to ambient temperature, was collected and dried to give crude 2-methyl-5-nitrophenol. This crude phenol (36.8 g) in dimethylformamide (200 ml) along with anhydrous $K_2CO_3$ (35 g) and 2-bromopropane (50 ml) was stirred and warmed to 60° C. for 12 hours. After cooling, the solvent was removed, the residue treated with water and the product extracted with ether. This ether solution was washed with 2N KOH, water, dried ($MgSO_4$) and evaporated to give 1-(1-methylethoxy)-2-methyl-5-nitrobenzene, bp. 80°-85° C./0.15 mm., 34.5 g. This nitrobenzene (34.5 g) in methanol (250 ml) was reduced on a parr hydrogenator using Raney nickel. After removal of the catalyst and solvent, the product, 3-(1-methylethoxy)-4-methyl-benzenamine, bp. 80°-85° C./0.05 mm., 25 g. was obtained. This amine (10 g) in methylene chloride (50 ml) and crushed ice (50 g) was stirred whilst thiophosgene (6.5 ml) in methylene chloride (25 ml) was added dropwise. The reaction was stirred overnight at ambient temperature. After separating the organic layer, the methylene chloride solution was washed with water, dried and evaporated to leave a pale yellow oil, bp. 80°-85° C./0.04 mm of 5-isothiocyanato-1-(methylethoxy)-2-methylbenzene, 12,4 g. Ethyl 3-amino-4,4,4-trifluoro-2-butenoate (11 g) was added portionwise to a stirred suspension of sodium hydride (2.5 g, 60%) in tetrahydrofuran (50 ml) at 15° C. When complete, the reaction was chilled to −70° C. (acetone/ dry ice), whereupon the above isothiocyanate (12.4 g.) in THF (25 ml) was added at once. The temperature rose to −50° C. before cooling to −70° C. After stirring to ambient temperature and leaving overnight a solid had precipitated out. The solvent was removed, water added, washed with ether and acidified. A pale yellow solid had precipitated out. This was collected on a filter, washed with water, dried and recrystallized from IPA to give 2,3 dihydro-3-[3-(1-methylethoxy)-4-methylphenyl]- 2-thioxo-6-(trifluoromethyl)-4(1H)-pyrimidinone, mp. 227°-228°.

EXAMPLE 2

3-λ4-Methyl-3-(2-propynyloxy)phenyl-6-(trifluoromethyl)-2,4-(1H,3H)pyrimidinedione (Compound No. 6)

As described above 1-methyl-4-nitro-2-(2-propynyloxy)benzene was made, mp 75°-77° C. This compound, (26 g) was reduced using iron in ethanol and water to give 4-methyl-3-(2-propynyloxy)benzenamine isolated as the hydrochloride salt mp >250° C. This amine salt was converted to the isocyanate analogue using phosgene in ethyl acetate as solvent, i.e. 4-isocyanato-4-methyl- 2-(2-propynyloxy)benzene, bp 78°-80° C./0.05 mm. Ethyl 3-amino-4,4,4-trifluoro-2-butenoate (19.6 g) was converted to its sodium salt using sodium hydride (4.6 g., 60%) in THF (100 ml). This solution was chilled to −62° C. and treated with a solution of the isocyanate (20 g) in THF (15 ml) over 2 minutes. The reaction warmed to −48° C. before cooling again. After stirring to ambient temperature and overnight the solvent was removed, water (250 ml) added, filtered to remove the precipitate and acidified whereupon a second precipitate was obtained. This solid was collected on a filter washed with water and re-extracted into aqueous sodium bicarbonate. After filtering the clear filtrate was acidified and the resulting cream precipitate was collected on a filter, washed with water and dried to give 3-[4-methyl-3-(2-propynyloxy)-phenyl]-6- (trifluoromethyl)-2,4-(1H,3H)-pyrimidinedione, mp 202°-204° C.

EXAMPLE 3

4-Chloro-2-fluoro-5-(2-propenyloxy)phenyl-6-(trifluoromethyl) 2,4-(1H,3H)pyrimidinedione (Compound No. 1)

This compound was made in a manner similar to the above compounds except that 1-chloro-5-fluoro-4-isocyanato-2-(2-prophenyloxy)benzene was used and the sodium salt of the uracil was isolated as a beige solid prior to its conversion to 4-chloro-2-fluoro-5-(2-pro penyloxy)phenyl-6-(trifluoromethyl)-2,4 (1H,3H)pyrmidinedione, mp 70°-73° C.

EXAMPLES 4-7

Preparation of Compound Nos. 2, 4, 5 and 7

Following the procedures of Examples 1-3, Compound numbers 2, 4, 5 and 7 were synthesized.

A summary of the compounds prepared, including Compound numbers 1, 3 and 6 are shown in Table I. All of the compounds gave satisfactory infrared and/or NMR spectra and/or elemental analysis (CH and N).

TABLE 1

| Cmpd. No. | R1 | R2 | R3 | R4 | R5 | R6 | R7 | X | Y | MP° C. |
|---|---|---|---|---|---|---|---|---|---|---|
| 1 | H | $CH_2CH=CH_2$ | Cl | H | H | H | $CF_3$ | O | O | 70-73 |
| 2 | H | $CH_3$ | $H_3$ | H | H | H | $CF_3$ | O | O | 145-148 |
| 3 | H | $CH(CH_3)_2$ | $CH_3$ | H | H | H | $CF_3$ | S | O | 227-228 |
| 4 | H | $CH(CH_3)_2$ | $CH_3$ | H | H | H | $CF_3$ | O | O | 151-154 |
| 5 | H | $CH_3$ | $OCH_3$ | $OCH_3$ | H | H | $CF_3$ | O | O | 221-224 |
| 6 | H | $CH_2C\equiv CH$ | $CH_3$ | H | H | H | $CF_3$ | O | O | 202-204 |
| 7 | H | $CH_2CO_2CH_2CH_3$ | $CH_3$ | H | H | H | $CF_3$ | S | O | 227-230 |

EXAMPLE 8

Preparation of Insecticidal Compositions

Each of Compounds Nos. 1-7 were formed into compositions. This was accomplished by dissolving 0.3 g. of each of the compounds in 10 ml of acetone to which was added four drops of ethoxylated sorbitan monolaurate, a wetting agent. Each of these solutions was diluted with water forming a 1,000 ppm suspension.

EXAMPLE 9

Rice Planthopper Foliar Test

One pot containing approximately 20 Mars variety rice seedlings was treated with each formulation at 1,000 ppm active concentration by spraying with a spray atomizer. One day after treatment, plants were covered with a tubular cage and twenty adult rice delphacids, *Sogatodes oryzicola*, were transferred into each cage.

Controls were also provided by duplicating this treatment except that the active compounds were not applied. The controls, however, included the placement on the control rice seedling plants, twenty adult rice planthoppers. Five days after transferring, counts were made of the surviving planthoppers in each pot and percent control was estimated in accordance with testing procedures well established in the art. The results of the testing of rice planthoppers (RPH) are given in Table II.

For comparative purposes and to illustrate the unexpected activity of the compounds, Table IIa gives the results of similar tests using the following compound analogs which are outside of this scope of this invention:

A) 1-methylethyl 5-(3,6-dihydro-2,6-dioxo-4-methyl-1(2H)-pyrimidinyl)-2-methylbenzoate;
B) 5-bromo-1,6-dimethyl-3-phenyl-2,4(1H,3H)-pyrimidinedione; and
C) 6-methyl-3-phenyl-2,4(1H,3H)-pyrimidinedione.

TABLE II

| Cmpd. No. | Estimated % Control RPH |
|---|---|
| 1 | 100 |
| 2 | 25 |
| 3 | 40 |

TABLE II-continued

| Cmpd. No. | Estimated % Control RPH |
|---|---|
| 4 | 45 |
| 5 | 45 |
| 6 | 80 |

TABLE IIa

| Compound | Compound Structure | Estimated % Control RPH |
|---|---|---|
| A | 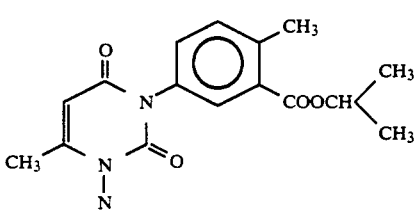 | 0 |
| B | 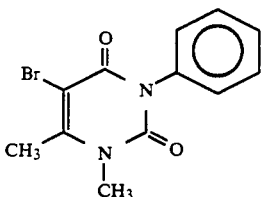 | 0 |
| C | 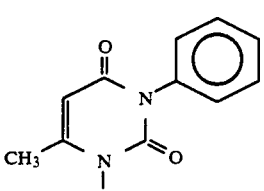 | 0 |

The above embodiments and examples are merely illustrative of the scope and spirit of the instant invention which is only limited by the appended claims.

We claim:

1. A compound of formula I:

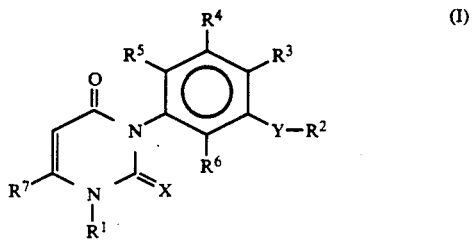

wherein $R^1$ is hydrogen, alkali or alkaline earth metal or organic base salts;

$R^2$ is $C_1-C_6$ hydrocarbyl or $-CR^8R^9-CO_2R^{10}$ wherein $R^8$ and $R^9$ are each independently hydrogen or linear or branched $C_1-C_4$ alkyl and $R^{10}$ is hydrogen or $C_1-C_6$ hydrocarbyl;

$R^3$ is hydrogen, $C_1-C_6$ hydrocarbyl, $C_1-C_6$ alkoxy, $C_1-C_6$ akylthio or $C_3-C_6$ cycloalkyl, with the proviso that when $R^3$ is hydrogen, $R^1$ is not hydrogen;

$R^4$, $R^5$ and $R^6$ are each independently hydrogen, halogen, $C_1-C_4$ alkyl or $C_1-C_4$ alkoxy;

$R^7$ is $C_1-C_6$ halogenated hydrocarbyl;

X and Y are each independently oxygen or sulfur.

2. A compound of claim 1 wherein:

$R^1$ is hydrogen or potassium;

$R^2$ is $C_1-C_4$ hydrocarbyl or $-C^8C^9-CO_2R^{10}$ wherein $R^8$ and $R^9$ are alkyl and $R^{10}$ is hydrogen or $C_1-C_4$ alkyl;

$R^3$ is hydrogen, halogen, $C_1-C_4$ alkyl, $C_1-C_4$ alkoxy or $C_1-C_4$ thioalkyl;

$R^4$, $R^5$ and $R^6$ are each independently hydrogen, halogen, $C_1-C_4$ alkyl or $C_1-C_4$ alkoxy;

$R^7$ is $C_1-C_3$ fluorinated alkyl;

X is oxygen or sulfur; and

Y is oxygen.

3. A compound of claim 1 wherein:

$R^1$ is hydrogen;

$R^2$ is $C_1-C_3$ hydrocarbyl or $-CH_2CO_2R^{10}$ wherein $R^{10}$ is $C_1-C_4$ alkyl;

$R^3$ is hydrogen, chloro, methyl or methoxy;

$R^4$, $R^5$ and $R^6$ are hydrogen, fluoro or methoxy;

$R^7$ trifluoromethyl;

X is oxygen or sulfur; and

Y is oxygen.

4. A composition having an activity selected from the group consisting of insecticidal, miticidal and nematicidal which comprises:

A) an effective amount of a compound having the following structure

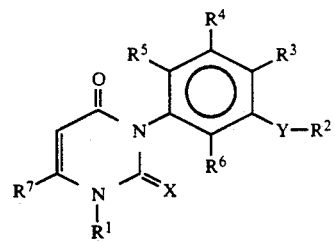

wherein $R^1$ is hydrogen, alkali or alkaline earth metal or organic base salts;

$R^2$ is $C_1-C_6$ hydrocarbyl or $CR^8R^9-CO_2R^{10}$ wherein $R^8$ and $R^9$ are each independently hydrogen or linear or branched $C_1-C_4$ alkyl and $R^{10}$ is hydrogen or $C_1-C_6$ hydrocarbyl;

$R^3$ is hydrogen, halogen, nitro, $C_1-C_6$ hydrocarbyl, $C_1-C_6$ alkoxy, $C_1-C_6$ alkylthio or $C_3-C_6$ cycloalkyl;

$R^4$, $R^5$ and $R^6$ are each independently hydrogen, halogen, $C_1-C_4$ alkyl or $C_1-C_4$ alkoxy;

$R^7$ is $C_1-C_6$ halogenated hydrocarbyl; and X and Y are each independently oxygen or sulfur; and B) a suitable carrier.

5. A composition according to claim 4 wherein $R^1$ is hydrogen or potassium;

$R^2$ is $C_1-C_4$ hydrocarbyl or $CR^8R^9-CO_2R^{10}$ wherein $R^8$ and $R^9$ are each independently hydrogen or linear or branched $C_1-C_4$ alkyl an $R^{10}$ is hydrogen or $C_1-C_4$ alkyl;

$R^3$ is hydrogen, halogen, $C_1-C_4$ alkyl, $C_1-C_4$ alkoxy or $C_1-C_4$ thioalkyl;

$R^4$, $R^5$ and $R^6$ are each independently hydrogen, halogen, $C_1-C_4$ alkyl or $C_1-C_4$ alkoxy;

$R^7$ is $C_1-C_3$ fluorinated alkyl;

X is oxygen or sulfur; and

Y is oxygen.

6. A composition according to claim 4 wherein $R^1$ is hydrogen;

$R^2$ is $C_1-C_3$ hydrocarbyl or $-CH_2CO_2R^{10}$ wherein $R^{10}$ is $C_1-C_4$ alkyl;

$R^3$ is hydrogen, chloro, methyl or methoxy;

$R^4$, $R^5$ and $R^6$ are hydrogen, fluoro or methoxy;

$R^7$ is trifluoromethyl;

X is oxygen or sulfur; and

Y is oxygen.

7. A method of controlling insects, mites and nematodes which comprises applying thereto an effective amount of the composition of claim 4.

8. A method of controlling insects, mites and nematodes which comprises applying thereto an effective amount of the composition of claim 5.

* * * * *